United States Patent [19]

Asada et al.

[11] Patent Number: 5,189,144

[45] Date of Patent: Feb. 23, 1993

[54] HUMAN CALPASTATIN-LIKE POLYPEPTIDE

[75] Inventors: Kiyozo Asada; Takashi Uemori; Masahiro Endo, all of Otsu; Fusao Kimizuka, Ohmihachiman; Ikunoshin Kato, Uji, all of Japan

[73] Assignee: Takara Shuzo Co., Ltd., Kyoto, Japan

[21] Appl. No.: 852,343

[22] Filed: Mar. 17, 1992

Related U.S. Application Data

[63] Continuation of Ser. No. 516,981, Apr. 30, 1990, abandoned.

[30] Foreign Application Priority Data

Apr. 28, 1989 [JP] Japan .................... 1-107388
May 22, 1989 [JP] Japan .................... 1-126648

[51] Int. Cl.$^5$ ............................... C07K 7/00
[52] U.S. Cl. ............................ 530/324; 530/350
[58] Field of Search ...................... 530/350, 324

[56] References Cited

U.S. PATENT DOCUMENTS 5,037,957 8/1991 Grubb et al. .................... 530/330

OTHER PUBLICATIONS

Asada et al., J. Enzyme Inhibition, 1989, vol. 3, pp. 49-56.
Emori et al., The Jour. of Biolog. Chem., vol. 263, No. 5 Feb. 15, 1988, pp. 2364-2370.
Kawasaki et al., J. Biochem., 106, 274-281 (1989).
Maki et al., J. Biolog. Chem., vol. 264, No. 32 Nov. 15, 1989, pp. 18866-18869.
Uemori et al., Biochemical and Biophysical Research Communications, vol. 166, No. 3 (1990) pp. 1485-1493.

Primary Examiner—Robert J. Hill, Jr.
Assistant Examiner—Shelly J. Guest
Attorney, Agent, or Firm—Wenderoth, Lind & Ponack

[57] ABSTRACT

Polypeptides are provided which have a calpain inhibitory activity. The polypeptides have an activity like that of natural human calpastatin but are significantly shorter in length than natural human calpastatin. The polypeptides are suited for synthetic manufacture.

1 Claim, 7 Drawing Sheets

|  | 70. | 80. | 90. | 100. | 110. | 120. | 130. | 140. | 150. |
|---|---|---|---|---|---|---|---|---|---|
| pHCSd18 | PSEKSAEPKTKPQDTVSAGGESVAGVAATSGKPGDKKKEKKSLTPAVPVESKPDKPSGKSGMDAALDDLIDTLGGPEETEEENTT |
| pHCSd42 | KSLTPAVPVESKPDKPSGKSGMDAALDDLIDTLGGPEETEEENTT |
| pHCSd94 | KSLTPAVPVESKPDKPSGKSGMDAALDDLIDTLGGPEETEEENTT |
| pHCSd65 | PDKPSGKSGMDAALDDLIDTLGGPEETEEENTT |
| pHCSd81 | PEETEEENTT |
| pHCSd421 | KSLTPAVPVESKPDKPSGKSGMDAALDDLIDTLGGPEETEEENTT |
| pHCSd422 | KSLTPAVPVESKPDKPSGKSGMDAALDDLIDTLGGPEETEEENTT |

|  | 160. | 170. | 180. | 190. | 200. | 210. | 220. | 230. | 240. |
|---|---|---|---|---|---|---|---|---|---|
| pHCSd18 | YTGPEVSDPMSSTYIEELGKREVTIPPKYRELLAKPIGPDDAIDALSSDFTCGSPTAAGKKTEKEESTEVLKAQSAGTVRSAAPPQEK |
| pHCSd42 | YTGPEVSDPMSSTYIEELGKREVTIPPKYRELLAKPIGPDDAIDALSSDFTCGSPTAAGKKTEKEESTEVLKAQSAGTVRSAAPPQEK |
| pHCSd94 | YTGPEVSDPMSSTYIEELGKREVTIPPKYRELLAKPIGPDDAIDALSSDFTCGSPTAAGKKTEKEESTEVLKAQSAGTVRSAAPPQEK |
| pHCSd65 | YTGPEVSDPMSSTYIEELGKREVTIPPKYRELLAKPIGPDDAIDALSSDFTCGSPTAAGKKTEKEESTEVLKAQSAGTVRSAAPPQEK |
| pHCSd81 | GPEVSDPMSSTYIEELGKREVTIPPKYRELLAKPIGPDDAIDALSSDFTCGSPTAAGKKTEKEESTEVLKAQSAGTVRSAAPPQEK |
| pHCSd421 | YTGPEVSDPMSSTYIEELGKREVTIPPKYRELLAKPIGPDDAIDALSSDFT |
| pHCSd422 | YTGPEVSDPMSSTYIEELGKREVTIPPKYRELLA |

Fig. 3

HUMAN CALPASTATIN-LIKE POLYPEPTIDE

This application is a continuation of now abandoned application, Ser. No. 07/516,981 filed on Apr. 30, 1990.

FIELD OF THE INVENTION

This invention relates to a novel peptide that inhibits the activity of human calpain, which has a variety of physiological activitives in the body.

DESCRIPTION OF THE PRIOR ART

Calpastatin is an intracellular protein that specifically inhibits calpain, which is a calcium-dependent cysteine protease. Calpastatin is found in the tissue of a wide variety of higher animals, and is activated to regulate the action of calpain by stimuli received by the cells. The function of calpain in the body is to activate kinase such as protein kinase C and phosphorylase kinase B by their limited degradation, and to decompose proteins of the cell skeleton and receptors of growth factors and hormones.

Calpastatin specifically inhibits these effects of calpain, thus regulating calpain and preventing its excessive functioning. The imbalance of the calpain-calpastatin system is closely related to certain disease states.

For example, in patients with muscular dystrophy, the level of calpain is high, and the degeneration of myofibrils and neurofilaments by calpain is accelerated, which seems to be related to the onset of this disease. Also, in cells infected with adult T-cell leukemia viruses, the activity levels of calpain and of receptors for interleukin 2 are abnormally high. These abnormalities suggest that change of the receptor activity for calpain affects proteins of the cell skeleton, and then the cells come to have an abnormal reaction to growth factors and the like, possibly causing the appearance of the disease (Y. Adachi et al., Seikagaku, 57, 1202, 1985). Further, calpain cleaves the protein of crystalline lens; when this reaction is excessive in its extent, it may cause cataracts. Also, calpastatin is identical to the stabilizing factor of steroid-receptor complexes that is required for the signal transduction (J. E. Bodwell et al., J. Biol. Chem., 260, 2601-2604, 1985). Also, in hypertensive rats, the calpastatin level is abnormally low (S. Pontremoli et al., Biochem. Biophys. Res. Commun., 145, 1287-12948 1987).

In these ways, calpastatin is an endogenous inhibitor of calpain that regulates its functioning, and it may be a useful drug for the treatment of diseases that seem to be caused by the excessive working of calpain.

The sequence of DNA that codes for human calpastatin can be used for the DNA diagnosis of a variety of diseases that may be caused by an imbalance in human calpain and human calpastatin.

Problems to be solved by the invention

Calpastatin is found in the tissues of higher animals, and it has been purified from porcine red blood cells and cardiac muscle and also from rabbit liver (M. Inomata et al., J. Biochem., 95, 1661-1670, 1984; E. Takano et al., Biohem. J., 235, 97-102, 1986; E. Takano et al., Biochem. Biophys. Res. Commun. 122, 912-917, 1984).

Calpastatin from swine and rabbits has had its cDNA cloned, and the primary structure of its amino acids has been identified (E. Takano et al., Biochemistry, 27, 1964-1972, 1988; Emori et al. Proc. Natl. Acad. Sci. U.S.A., 84, 3590-3594, 1987). The basic structure of calpastin from these two species is held in common, with four repeating functional units (domains 1-4) each containing about 140 amino acid residues and a non-homologous sequence on the N-terminal side, named domain L (M. Maki et al., FEBS Lett., 223, 174-180, 1987).

The inventors of this invention have identified the primary structure of domains 1-4 of human calpastatin (Japanese Patent Application 63-109111) filed May 6, 1988 and also the entire structure (Japanese Patent Application 63-207283, filed Aug. 25, 1988. The purpose of the present invention is to provide a polypeptide with a relatively short chain that has the various activities of human calpastatin.

SUMMARY OF THE INVENTION

Briefly, this invention relates to a human calpastatin-like polypeptide that has the following amino acid sequence [I].

A—Thr—Tyr—Ile—Glu—Glu—Leu—Gly—Lys—Arg—Glu—Val—Thr—Ile—Pro—Pro—Lys—Tyr—Arg—B   [I]

wherein A is of the following sequence:

Pro—Ser—Glu—Lys—Ser—Ala—Glu—Pro—
Lys—Thr—Lys—Pro—Gln—Asp—Thr—Val—Ser—Ala—
Gly—Gly—Glu—Ser—Val—Ala—Gly—Val—Ala—Ala—
Thr—Ser—Gly—Lys—Pro—Gly—Asp—Lys—Lys—Lys—
Glu—Lys—Lys—Ser—Leu—Thr—Pro—Ala—Val—Pro—
Val—Glu—Ser—Lys—Pro—Asp—Lys—Pro—Ser—Gly—
Lys—Ser—Gly—Met—Asp—Ala—Ala—Leu—Asp—Asp—
Leu—Ile—Asp—Thr—Leu—Gly—Gly—Pro—Glu—Glu—
Thr—Glu—Glu—Glu—Asn—Thr—Thr—Tyr—Thr—Gly—
Pro—Glu—Val—Ser—Asp—Pro—Met—Ser—Ser or is of this sequence with a deletion of an amino acid or a peptide from the N-terminal end, and wherein B is of the following sequence:

Glu—Leu—Leu—Ala—Lys—Pro—Ile—Gly—Pro—Asp—
Asp—Ala—Ile—Asp—Ala—Leu—Ser—Ser—Asp—Phe—
Thr—Cys—Gly—Ser—Pro—Thr—Ala—Ala—Gly—Lys—
Lys—Thr—Glu—Lys—Glu—Glu—Ser—Thr—Glu—Val—
Leu—Lys—Ala—Gln—Ser—Ala—Gly—Thr—Val—Arg—
Ser—Ala—Ala—Pro—Pro—Gln—Glu—Lys— or of this sequence with a deletion of an amino acid or a peptide from the C-terminal end.

This invention also relates to a human calpastatin-like polypeptide having the following sequence [II].

C—Asp—Pro—Met—Ser—Ser—Thr—Tyr—Ile—Glu—Glu—   [II]
Leu—Gly—Lys—Arg—Glu—Val—Thr—Ile—Pro—
Pro—
Lys—Tyr—Arg—Glu—Leu—Leu—D wherein C is of the following sequence:

Pro—Ser—Glu—Lys—Ser—Ala—Glu—Pro—
Lys—Thr—Lys—Pro—Gln—Asp—Thr—Val—Ser—Ala—
Gly—Gly—Glu—Ser—Val—Ala—Gly—Val—Ala—Ala—
Thr—Ser—Gly—Lys—Pro—Gly—Asp—Lys—Lys—Lys—
Glu—Lys—Lys—Ser—Leu—Thr—Pro—Ala—Val—Pro—
Val—Glu—Ser—Lys—Pro—Asp—Lys—Pro—Ser—Gly—
Lys—Ser—Gly—Met—Asp—Ala—Ala—Leu—Asp—Asp—
Leu—Ile—Asp—Thr—Leu—Gly—Gly—Pro—Glu—Glu—
Thr—Glu—Glu—Glu—Asn—Thr—Thr—Tyr—Thr—Gly—
Pro—Glu—Val—Ser or is of this sequence with a deletion of an amino acid or a peptide from the N-terminal end, and D is of the following sequence:

Ala—Lys—Pro—Ile—Gly—Pro—Asp—Asp—Ala—Ile—
Asp—Ala—Leu—Ser—Ser—Asp—Phe—Thr—Cys—Gly—
Ser—Pro—Thr—Ala—Ala—Gly—Lys—Lys—Thr—Glu—
Lys—Glu—Glu—Ser—Thr—Glu—Val—Leu—Lys—Ala—
Gln—Ser—Ala—Gly—Thr—Val—Arg—Ser—Ala—Ala—
Pro—Pro—Gln—Glu—Lys— or of this sequence with a deletion of an amino acid or a peptide from the C-terminal end, but in which at least one of the two sequences C or D is present, so that not all of C has been deleted, or else not all of D has been deleted.

This invention also relates to a base sequence which codes for the polypeptide having the amino acid sequence [II] and to a recombinant plasmid which contains DNA which codes for the above mentioned polypeptide.

This invention also relates to a transformant which carries the above mentioned recombinant.

This invention also relates to a method for the preparation of a human calpastatin-like polypeptide which comprises the cultivation of the above mentioned transformant and recovery of the polypeptide having the amino acid sequence [II] from the culture broth.

This invention further relates to a human calpastatin-like polypeptide of the following sequence [III]:

E—Thr—Tyr—Ile—Glu—Glu—Leu—Gly—Lys—Arg—Glu—  [III]
Val—Thr—Ile—Pro—Pro—Lys—Tyr—Arg—F wherein E is the sequence Asp-Pro-Met-Ser-Ser or else this sequence with a deletion of an amino acid or a peptide from the N-terminal end, and F is the sequence Glu-Leu-Leu or else this sequence with a deletion of an amino acid or a peptide deleted from the C-terminal end.

We have selected a cDNA clone that codes for human calpastatin from a human cDNA library, and identified the entire amino acid sequence of human calpastatin by the analysis of that base sequence. Also, we have linked said cDNA to an expression vector, and introduced the vector into *Escherichia coli*, thereby bringing about the expression of a human calpastatin-like polypeptide.

We have used the methods of peptide synthesis (mentioned herein after) to synthesize a polypeptide of 18 amino acids in the domain of human calpastatin (i.e. the polypeptide of 18 amino acids of the sequence [III] with E and F deleted, hereinafter referred to as the polypeptide of 18 amino acids), a polypeptide of 21 amino acids (i.e. the polypeptide of 21 amino acids of sequence [III] with E deleted and F equal to Glu-Leu-Leu, hereinafter referred to as the polypeptide of 21 amino acids), and a polypeptide of 26 amino acids (i.e. the polypeptide of 26 amino acids of sequence [III] with E equal to Asp-Pro-Met-Ser-Ser and F equal to Glu-Leu-Leu, hereinafter referred to as the polypeptide of 26 amino acids), and found that these polypeptides can inhibit calpain.

This invention is based on these findings.

By the cloning of cDNA for human calpastatin, the primary structure of the amino acids was identified, and found to consist of four repeating functional units (domains 1–4) that consists of about 140 amino acid residues each, plus a non-homologous sequence named domain L on the N-terminal side (Japanese Laid-Open Patent Application 63-207283). Each of the domains 1–4 by itself has calpastatin activity, but the activity of domain 1 is the strongest, and therefore this domain was analyzed in more detail. It has been found that the polypeptide of 18 amino acids in domain 1 still has activity even after being shortened to such length.

The polypeptides longer than the polypeptide of 26 amino acids were prepared as described below by the techniques of genetic engineering.

Well-known methods can be used for the cloning of cDNA that codes for human calpastatin. For example, it is possible to extract RNA that contains poly A from established cell line of human origin or from liver or heart muscle where human calpastatin is distributed, and this can be purified on Sepharose as a carrier linked with oligo-dT. This can be used as a template in the synthesis of cDNA by the use of reverse transcriptase, and the cDNA synthesized can be joined with a plasmid or phage vector by a method such as that of Okayama-Berg or that of Gubler-Hoffmann. The vector can be introduced into a host, and a cDNA library prepared. This kind of library is available commercially, and can be obtained from, for example, CLONTECH Laboratories, Inc. When one portion of cDNA has already been obtained, a cDNA library can be prepared by the method of primer extension. This method is particularly useful for the cloning of the 5' end of cDNA.

In the screening for a cDNA clone that codes for the desired human calpastatin from a cDNA library, it is effective to use as a probe cDNA fragments of porcine or rabbit calpastatin, the sequences of which are already known. The DNA probe can be synthesized chemically, and it is also possible to cut it from a vector that contains cDNA by the use of restriction enzymes.

In the step of screening of a library with a DNA probe, the library must first be cultivated on a plate, and the colonies and plaques that grow are transferred to a nitrocellulose or nylon filter, after which the DNA is fixed to the filter by treatment that causes its denaturation. This filter is incubated in a solvent that contains DNA labelled with $^{32}P$ or the like, and the DNA on the filter and the probe DNA are hybridized (below, this step is called hybridization). The temperature of the incubation is generally set at the melting temperature, Tm, of the probe used. After hybridization, nonspecifically adsorbed substances are removed by washing, and the clones that are hybrids with the probe are identified by the use of autoradiography. This step is repeated to isolate a clone, which is next analyzed.

When the recombinant is *E. coli*, a small inoculum is cultured in a test tube or the like, and plasmids are extracted by the usual method and cleaved with restriction enzymes. Then the fragments obtained are treated by electrophoresis on agarose or polyacrylamide gels, and the production of the inserted fragments that is cloned is checked for. The electrophoresis pattern is transferred to a nitrocellulose or nylon filter, and by the method described above, the formation of a hybrid of the DNA probe and the inserted fragments is investigated. Finally, the base sequence of the inserted fragments is identified by the usual method. When the recombinant is a phage, basically the same steps of analysis of the clones are used. The cloned phage is used to infect host cells of *E. coli* in cultivation, and phage DNA is purified from the phage lysate. When the phage is λgt11, first, lysogenic bacteria are cultivated, and then phage lysate can be obtained by the use of a temperature shift. It is also possible to recover DNA from an infected plate. Details of the purification of phage DNA are given on, for example, page 76-85 of "Molecular Cloning: A Laboratory Manual (T. Maniatis et al., Cold Spring Harbor Laboratory, 1982)". The phage DNA can be cleaved with restriction enzymes and treated by gel electrophoresis to check that fragments have been inserted, or, by the use of hybridization, it is possible to study the homology with the cDNA for porcine calpastatin. Finally, by the identification of the base sequence, cloning is verified.

The base sequence found can be compared to the sequences published for rabbit and porcine cDNA, and the results can be used to find the structure of the gene and the amino acid sequence.

Or, by comparison with the functional units of porcine or rabbit calpastatin, it is possible to identify the functional units of human calpastatin.

In this way, it is possible to identify the DNA sequence that corresponds to the amino acid sequences of the functional units, domains 1, 2, 3 and 4, of human calpastatin. For porcine calpastatin, each of the functional units by itself can independently inhibit calpain, but the non-homologous sequence at the N-terminal side, functional domain L, does not have activity by itself. The same results are likely to be found for human calpastatin. Therefore, the entire gene structure of the cDNA that is obtained, or a DNA sequence that contains at least one of the functional domains 1-4, or a DNA sequence that has the region necessary for the maintenance of activity, and from which one part or all of the 5' side or the 3' side has been deleted is introduced into appropriate host cells by being joined to an expression vector, so that it is expressed, and these host cells are cultivated, so that a polypeptide that has the activity of human calpastatin will be produced. Any of the known kinds of vectors can be used as the expression vector.

It is known from experiments with the expression of porcine and rabbit calpastatin in *E. coli* that their molecules do not include any S-S bonds and also that their molecules do not contain any sugar chains. Thus, human calpastatin-like peptide can be expressed in *E. coli* in the same way.

Confirmation of expression can be done by the measurement of the inhibition of calpain, as in the measurement done with casein as the substrate, with extraction from a culture fluid of *E. coli*, and measurement of the decrease in the acid-soluble fraction by the use of spectroscopy.

Purification of human calpastatin-like polypeptide from *E. coli* can be done by ordinary chromatography. That is, the cultured cells can be treated with lysozyme, and is then sonicated, after which the supernatant is obtained, and the stability of calpastatin to heat treatment is use to obtain the acid-soluble fraction. Next, ion-exchange chromatography is used, followed by gel filtration and such chromatographic methods to obtain the desired peptide.

The above-mentioned preparation of the polypeptides of 26 amino acids in length or shorter may be done by the peptide synthetic methods as described below.

Thus the polypeptides can be synthesized chemically by the synthetic method that makes use of Fmoc (9-fluorenylmethoxycarbonylpolyamide; L. A. Carpino et al., J. Org. Chem., 37, 3404-3409, 1972; E. Atherton et al. J. Chem. Soc., Chem. Comm., 1978, 537-539, 1978; and J. Meienhofer et al., Int. J. Peptide Protein Res., 13, 35-42, 1979). The polypeptide that was synthesized inhibited calpain, which showed that a polypeptide of 18 amino acids could have calpastatin-like activity. Also, a polypeptide of 21 amino acids and a polypeptide of 26 amino acids had calpastatin-like activity.

As described above, with this invention, it is possible to provide human calpastatin-like polypeptides with the primary structure, functional units, and regions needed for the maintenance of activity between functional units needed for activity, and to provide means by which these polypeptides can be prepared by means of genetic engineering or by chemical methods.

BRIEF DESCRIPTION OF THE FIGURES

FIG. 1 shows the scheme for the construction of expression plasmids. Open boxes represent calpastatin cDNA segments.

DESCRIPTION OF THE PREFERRED EMBODIMENTS

The invention will be explained by reference to examples, but this invention is not to be taken to be limited to these examples.

Example 1

Production of calpastatin-like peptides by means of genetic engineering

1. Construction of expression plasmids:

The expression plasmids were constructed as shown in FIG. 1. The BamHI-AccI fragment of λcs131 (K. Asada et al., J. Enzyme Inhib., 3, 49-56, 1989) containing cDNA coding for parts of the domain L and domain 1 regions of calpastatin was ligated with the AccI-EcoRI fragment of λcs19 (K. Asada et al., J. Enzyme Inhib., 3, 49-56, 1989) containing cDNA coding for parts of domain 1 and domains 2-4 at the AccI site and inserted at the BamH1-EcoR1 polylinker region of pUC119N (Takara Shuzo).

The plasmid we constructed, designated pHCS13, was digested with BamH1, converted to flat ends by a fill-in reaction, and attached to NcoI linker (5'CAGCCATGGCTG3'). The molecules obtained were digested with NcoI and self-ligation was done, giving pHCS121. The NcoI-EcoRI fragment of pHCS121 containing calpastatin cDNA and the EcoRI-SalI fragment of a pINIII-ompAI vector (K. Nakamura et al., Cell, 18, 1109-1117, 1979), J. Ghrayeb et al., The EMBO J., 3, 2437-2442, 1984) containing the transcription terminator region of the outer membrane lipoprotein were ligated at the EcoRI site and inserted at the NcoI-SalI polylinker region of pUC118N to give pHCS131.

pHCS131 was digested with NcoI, converted to flat ends by a fill-in reaction, and digested with XhoI. The NcoI-XhoI fragment containing the vector region was isolated and designated fragment 1. The EcoRI insert containing the coding sequence of human calpastatin was isolated from λcs143 and digested with HinfI. The HinfI fragments generated were converted to flat ends by a fill-in reaction and digested with BcnI, and the fragment containing cDNA coding for domain L was isolated and designated fragment 2. The NcoI-XhoI fragment containing cDNA coding for parts of domain L and domain 1 was obtained from pHCS121 and digested with BcnI. The BcnI-XhoI fragment containing cDNA coding for domain 1 was isolated and designated fragment 3. The fragments 1, 2, and 3 were mixed and ligated to generate pHCS 181.

pHCS181 was digested with SacI and XbaI and treated with SI nuclease; self-ligation was performed, giving pHCS82, from which the cDNA coding for most of domain 2 and all of domains 3 and 4 had been removed. AvaIII and ClaI sites were introduced at the 5'-terminal side of the region coding for domain L by site-directed mutagenesis by use of a mutan K kit (Takara Shuzo) to give pHCS83; the oligonucleotides 5'TATCTGATGCATGCTTGGGTA3' and 5'GTGAGCATCGATACTTCCTG3', which can form base-pairs at positions 131 to 151, except for position 141 (C-T), and at 152 to 171, except for position 161 (T-T), were used for the introduction of the AvaIII and ClaI sites, respectively. pHCS83 was used to introduce a stop codon at the 3' terminal site of the region coding for domain 1, giving pHCS84, in the same way as the introduction of the AvaIII or ClaI site; the oligonucleotide 5'CCTTTCTTTACTTCTCTTG3' can form base-pairs at positions 718 to 736, except for position 727 (T-T). The AvaIII-SalI fragment was isolated from pHCS84 and inserted at the PstI-SalI polylinker region of pTV119N to give pHCS231. The *Escherichia coli* JM109 cells that carry plasmid were designated *E. coli* JM109/pHCS231. The strain was deposited at the Fermentation Research Institute of the Agency of Industrial Science and Technology, Japan, under FERM BP-2829.

Figure 2:
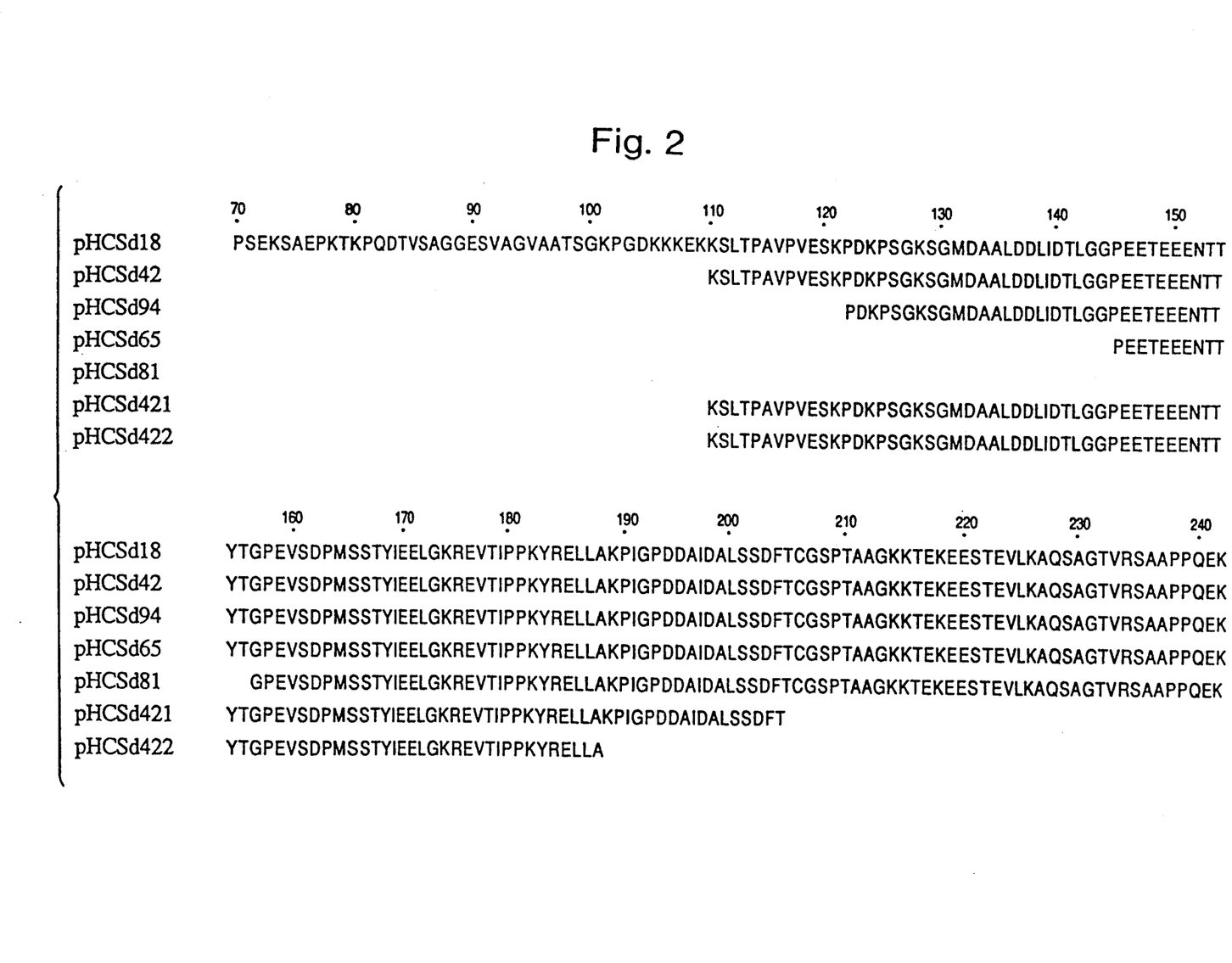
FIG. 2 shows amino acid sequences of the 7 truncated segments of human calpastatin. Amino acid residues are numbered (shown above the sequences) starting from the amino terminal end of human calpastatin.

The plasmid obtained, pHCS231, was digested with SphI and ClaI, and different sizes of DNA were deleted from the ClaI site in five progressively changed sets of conditions by use of a kilo-sequence deletion kit (Takara Shuzo). The molecules generated were then ligated with NcoI linkers (a mixture of 5'CAGC-CATGGCTG3', 5'AGCCATGGCT3', and 5'GCCATGGC3') and digested with NcoI before self-ligation was done. pHCSd18, pHCSd42, pHCSd94, pHCSd65, and pHCSd81 were among the plasmids constructed in this step (FIG. 2). Stop codons were introduced in pHCSd42 at nucleotide positions 616–618 with the oligonucleotide 5'TTCACCT-GAGGGTCGCC3' for the construction of pHCSd421 and at positions 565–567 with 5'TATTGGCTTAACC-CATA3' for the construction of pHCSd422 in the same way.

2. Preparation of calpastatin segments produced in *E. coli:*

*E. coli* 545πHR1 cells transformed with recombinant plasmids were cultured in LB medium to the late log phase and harvested. Cells were washed and suspended in one twenty-fifth the culture volume of 20 mM MES buffer (pH 5.5) containing 1 mM EDTA, 5 mM 2-mercaptoethanol, and 4 μM p-amidinophenylmethanesulfonylfluoride (A-PMSF). Crude extract was prepared by lysozyme treatment and freeze-thawing as described by M. Maki et al. (Biochem. Biophys. Res. Commun. 143, 300–308, 1987). For large-scale preparation, cells were lysed by sonication (twice, for 3 min each time). After treatment at 95° C. for 10 min, the lysate was centrifuged at 12,000 rpm (No. 5N, Tomy Seiko Co., Ltd., Tokyo, Japan) for 30 min at 4° C., and the supernatant was stored at −80° C. until further purification. The samples were partially purified by DEAEToyopearl chromatography. The column was previously equilibrated with 20 mM MES buffer (pH 5.5) containing 50 mM NaCl, 1 mM EDTA, and 4 μM A-PMSF, and elution was with a linear gradient of NaCl from 50 to 250 mM. The fractions containing inhibitory activity were assayed as described below, collected, and then purified by gel filtration on a column of Sephadex G-50 equilibrated with water to remove contaminating salts and nucleotides. The fractions containing calpastatin segments were detected by SDS-polyacrylamide gel electrophoresis and lyophilized. The segments were hydrolyzed, and their yields were measured and their purity was checked (amino acid analyzer L-8500, Hitachi, Tokyo, Japan).

EXAMPLE 2

Synthesis of a polypeptide of 18 amino acids, a polypeptide of 21 amino acids, and a polypeptide of 26 amino acids Starting materials:
Fmoc-Asp(OBut)-PFP
Fmoc-Pro-PFP
Fmoc-Met-PFP
Fmoc-Ser(But)-DHBT
Fmoc-Thr(But)-DHBT
Fmoc-Tyr(But)-PFP
Fmoc-Ile-PFP
Fmoc-Glu(OBut)-PFP
Fmoc-Leu-PFP
Fmoc-Gly-PFP
Fmoc-Lys(Boc)-PFP
Fmoc-Arg(Mtr)-DHBT
Fmoc-Val-PFP
Fmoc-Arg(Mtr)-OH
Fmoc-Leu-OH Here, but is t-butyl, PFP is pentafluorophenyl, DHBT is 1-oxo-2-hydroxydihydrobenzotriazine, Mtr is 4-methoxy-2,3,6-trimethylphenylsulfonyl, and Boc is t-butoxycarbonyl.

Resin: PepSyn TM KA (MilliGen)

1. Binding to resin and peptide elongation of Fmoc-Leu-OH, which is modified to become the C-terminal amino acid of the polypeptide with 18 amino acids, of the polypeptide with 21 amino acids, and of the polypeptide with 26 amino acids.

(1) Synthesis of an anhydride of [Fmoc-Arg(Mtr)]$_2$O and an anhydride of (Fmoc-Leu)$_2$O.

First, 730 mg of Fmoc-Arg(Mtr)-OH was dissolved in 5 ml of methylene chloride, and to the solution, 110 mg of dicyclohexylcarbodiimide was added. The mixture was agitated in an ice bath for 40 min, and then the dicyclourea was removed by filtration and concentrated to dryness under reduced pressure. The same procedure was done with the use of 420 mg of Fmoc-Leu-OH.

(2) Binding of [Fmoc-Arg(Mtr)]$_2$O and (Fmoc-Leu)$_2$O to resin (PepSyn TM KA).

First, 720 mg of the anhydride of [Fmoc-Arg(Mtr)]$_2$O was dissolved in enough dimethylformamide (DMF) to get wet the resin, and in the presence of 11 mg of 4-dimethylaminopyridine, 1 g of resin was allowed to react for about 2 hr. After the end of the reaction, the reaction mixture was washed first with 10 ml of DMF and then with 10 ml of methylene chloride, after which the mixture was dried. The binding rate was checked by amino acid analysis. Separately, an anhydride of 410 mg of (Fmoc-Leu)₂O was treated in the same way.

(3) Elongation of peptide chain.

Next, the synthesized Fmoc-Arg(Mtr)-PepSyn T-M KA resin was used to fill a column for use in a peptide synthesizer (MilliGen), and a peptide synthesizer (MilliGen) was used to add Fmoc-Tyr(But)-PFP, Fmoc-Lys(Boc)-PFP, and so on, in order, up to the 18th compound Fmoc-Thr(But)-DHBT, to the C-terminal end of a polypeptide, so as to synthesize the polypeptide of 18 amino acids. Also, the Fmoc-Leu-PepSyn TM KA resin was bound with Fmoc-Leu-PFP, Fmoc-Glu(OBut)-PFP, and so on, in order, up to the 21st Fmoc-Thr(But)-DHBT, to form the polypeptide with 21 amino acids, and up to the 26th compound, Fmoc-Asp(OBut)-PFP, to form the polypeptide with 26 amino acids. After the end of synthesis, the resin that was bound to the peptide was washed with 10 ml of methylene chloride (4 times), with 10 ml of t-amyl alcohol (2 times), 10 ml of acetic acid (2 times), and 10 ml of diethyl ether (4 times).

2. Removal of resin and protective groups:

At the end of synthesis, 20% piperidine DMF was added to the resin and the mixture was left for 1 hour, after which 10 ml of DMF was used to wash the resin, followed by 10 ml of methylene chloride. Then the resin was dried. To the residue was added 10 ml of a 90:5:5 mixture of trifluoroacetate (TFA), ethanedithiol, and thioanisole. The mixture was left for 3 hours. Next, water was added so that the concentration of the TFA would be 5%, and the mixture was washed first with 10 ml of hexane and then with 10 ml of ether. After the washing, water was removed with an evaporator, the residue was dissolved in 1 ml of 1N acetic acid, and one portion was treated by high-pressure liquid chromatography (column, YMC-ODS₅C₁₈, mobile phase, 0.05% TFA in water—0.05% TFA in acetonitrile). The fractions at the peaks eluted were analyzed for their amino acids. The fractions with the correct amino acid composition were collected, and their molecular weights were estimated by use of fast atom bombardment mass spectroscopy to check whether the protective groups had been removed. In this way, 32 mg of the polypeptide with 18 amino acids, 40 mg of the polypeptide with 21 amino acids, and 50 mg of the polypeptide with 26 amino acids were obtained.

EXAMPLE 3

Detection of inhibition of calpain by calpastatin-like polypeptides:

The assay of calpain inhibition was done as described below (A. Kitahara et al., J. Biochem., 95, 1759–1766, 1984). First, 10 µl of the sample 2.5 µl of calpain at the concentration of 1 mg/ml, 40 µl of 2% casein in imidazole, and 20 µl of crysteine at the concentration of 6 mg/ml were mixed together, giving a total volume of 180 µl. Next, the mixture was treated for 5 min at 30° C., after which 20 µl of 50 mM calcium chloride was added, and the mixture was incubated for 15 min at 30° C. Then 200 µl of 5% trichloroacetic acid was added to stop the reaction, and the mixture was centrifuged at 12,000 rpm for 10 min. The supernatant was obtained, and its absorbance at 280 nm was measured, from which the inhibitory activity toward calpain was calculated.

Figure 3:
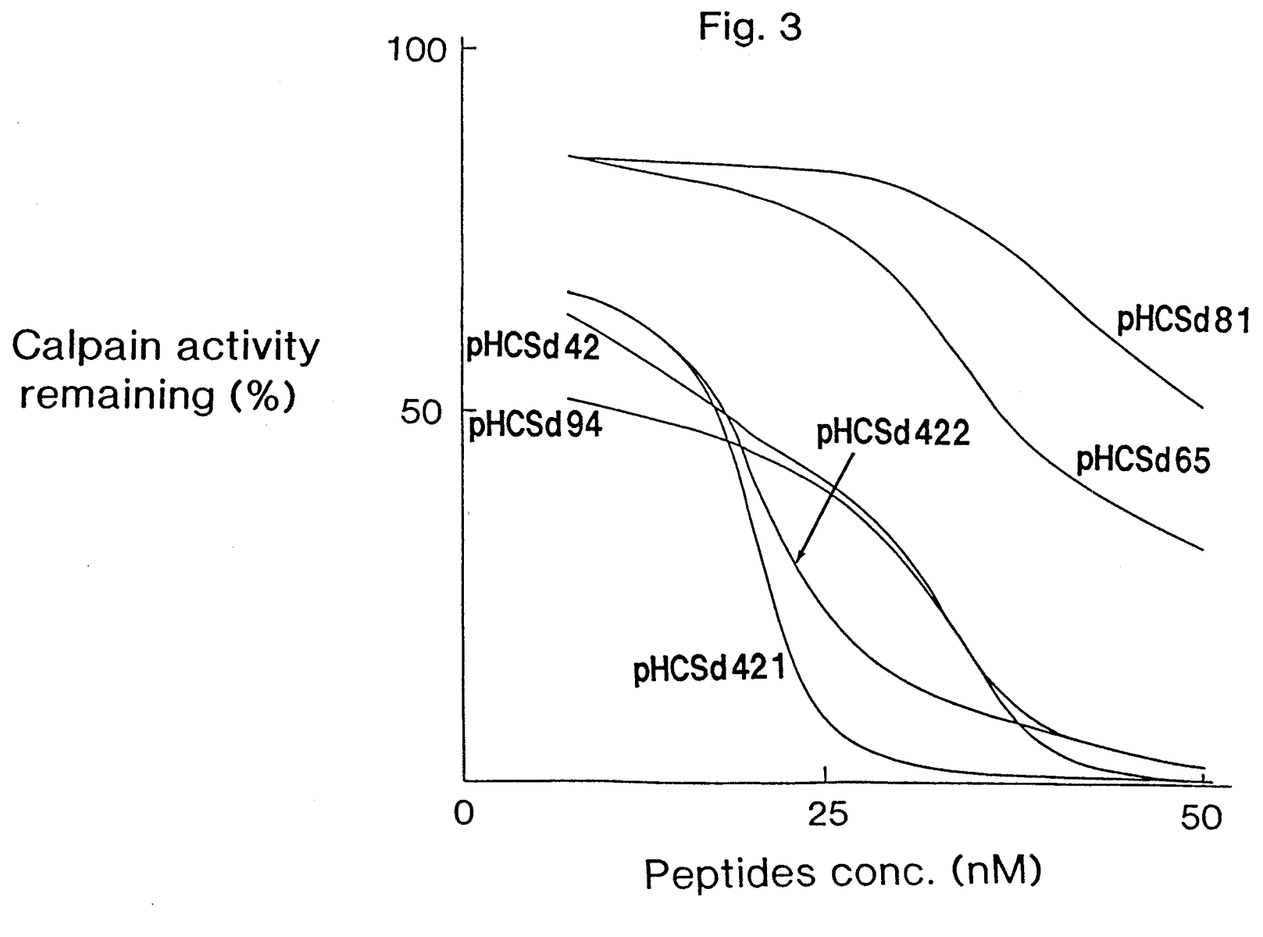
FIG. 3 shows the profile of the inhibition of calpain by calpastatin segments produced in *E. coli* 545 πHR1. Name of the expression plasmid is shown for each corresponding segment.
Figure 4:
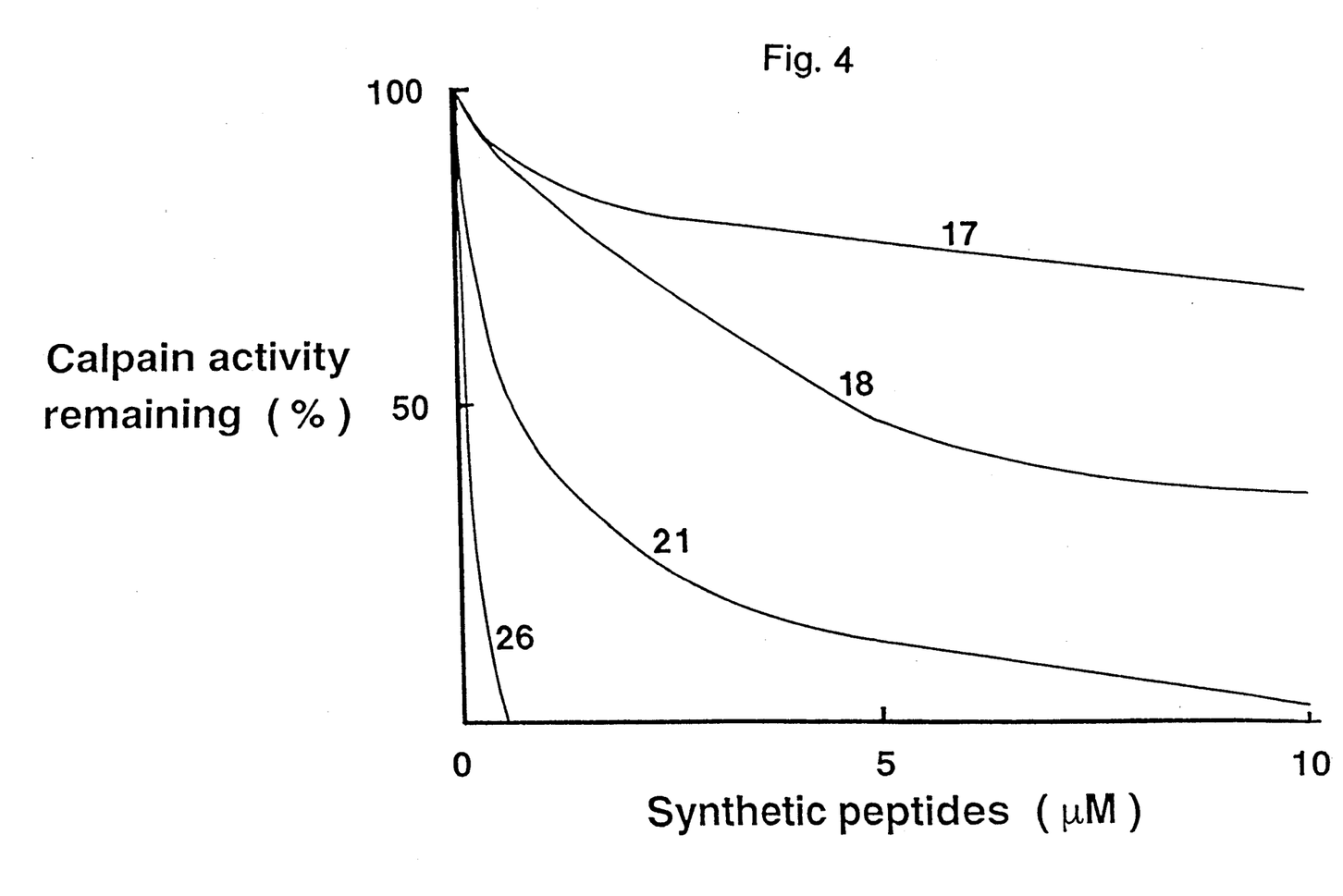
FIG. 4 shows the profile of the inhibition of calpain by synthetic calpastatin segments. Number of amino acid residues for each segment is shown above the corresponding curve.

The results are shown in FIGS. 3 and 4. The calpastatin-like polypeptides produced in Example 1 and synthesized in Example 2 inhibited calpain.

COMPARATIVE EXAMPLE 1

Detection of inhibition of calpain by a polypeptide with an amino acid or peptide from the N-terminal of the polypeptide with 18 amino acids:

(1) Synthesis of polypeptides with deletion at the N-terminal

By the procedure shown in Example 2, to the Fmoc-Arg(Mtr)-PepSyn TM KA resin, Fmoc-Tyr(But)-PFP, Fmoc-Lys(Boc)-PFP and a total of 11 compounds were bound, giving a synthetic polypeptide ending with Fmoc-Lys(Boc)-PFP. Also, a similar polypeptide was made with 12 compounds ending in Fmoc-Gly-PFP. A similar polypeptide was made with 13 compounds ending in Fmoc-Leu-PFP. A similar polypeptide was made with 14 compounds ending in Fmoc-Glu(OBut)-PFP. A similar polypeptide was made with 15 compounds ending in Fmoc-Glu(OBut)-PFP. A similar polypeptide was made with 16 compounds ending in Fmoc-Ile-PFP. A similar polypeptide was made with 17 compounds ending with Fmoc-Tyr(But)-PFP.

(2) Detection of inhibition of calpain:

These synthetic polypeptides were used in an assay for calpain inhibition by the procedures in Example 3. The results showed that these polypeptides with these deletions at the N-terminal had very little or no inhibitory activity toward calpain. The inhibitory activity of the polypeptide with 17 amino acids is shown in FIG. 4. Thus, the strength of this activity was almost undetectable.

The results described above shows that this invention provides novel polypeptides with human calpastatin-like activity. These novel polypeptides may have effects on various disorders that seem to originate in the excess activity of calpain.

What we claim is:

1. A polypeptide having a calpain inhibitory activity and having the following amino acid sequence:

Lys—Ser—Leu—Thr—Pro—Ala—Val—Pro—Val—Glu—

Ser—Lys—Pro—Asp—Lys—Pro—Ser—Gly—Lys—Ser—

Gly—Met—Asp—Ala—Ala—Leu—Asp—Asp—Leu—Ile—

Asp—Thr—Leu—Gly—Gly—Pro—Glu—Glu—Thr—Glu—

Glu—Glu—Asn—Thr—Thr—Tyr—Thr—Gly—Pro—Glu—

Val—Ser—Asp—Pro—Met—Ser—Ser—Thr—Tyr—Ile—

Glu—Glu—Leu—Gly—Lys—Arg—Glu—Val—Thr—Ile—

Pro—Pro—Lys—Tyr—Arg—Glu—Leu—Leu—Ala—Y, wherein Y is selected from the group consisting of —OH and —Lys—Pro—Ile—Gly—Pro—Asp—Asp—Ala—Ile—Asp—

Ala—Leu—Ser—Ser—Asp—Phe—Thr.

* * * * *